(12) United States Patent
Woo et al.

(10) Patent No.: US 9,470,635 B2
(45) Date of Patent: Oct. 18, 2016

(54) SYSTEM OF MEASURING WARPAGE AND METHOD OF MEASURING WARPAGE

(71) Applicant: SAMSUNG ELECTRO-MECHANICS CO., LTD, Suwon-si, Gyeonggi-do (KR)

(72) Inventors: Seung Wan Woo, Suwon-si (KR); Young Nam Hwang, Suwon-si (KR); Po Chul Kim, Suwon-si (KR); Kyung Ho Lee, Suwon-si (KR); Suk Jin Ham, Suwon-si (KR)

(73) Assignee: Samsung Electro-Mechanics Co., Ltd., Suwon-si (KR)

( * ) Notice: Subject to any disclaimer, the term of this patent is extended or adjusted under 35 U.S.C. 154(b) by 373 days.

(21) Appl. No.: 14/048,703

(22) Filed: Oct. 8, 2013

(65) Prior Publication Data

US 2014/0104417 A1   Apr. 17, 2014

(30) Foreign Application Priority Data

Oct. 12, 2012   (KR) .................. 10-2012-0113554

(51) Int. Cl.
*G01N 21/88* (2006.01)
*G01B 11/30* (2006.01)
*G01N 25/16* (2006.01)

(52) U.S. Cl.
CPC ............. *G01N 21/88* (2013.01); *G01B 11/306* (2013.01); *G01N 25/16* (2013.01)

(58) Field of Classification Search
CPC ................................................ G01B 11/306
See application file for complete search history.

(56) References Cited

U.S. PATENT DOCUMENTS

| | | | |
|---|---|---|---|
| 7,230,722 B2 | 6/2007 | Han et al. | |
| 8,444,462 B2 * | 5/2013 | Livchak | F24C 15/20 126/299 D |
| 2003/0060575 A1 * | 3/2003 | Caruso | C08G 64/06 525/462 |
| 2004/0170368 A1 * | 9/2004 | Childs | G02B 6/105 385/129 |
| 2005/0219553 A1 * | 10/2005 | Kelly | G01B 11/16 356/605 |
| 2010/0091302 A1 * | 4/2010 | Kim | G01B 11/2531 356/603 |
| 2011/0036822 A1 * | 2/2011 | Johnson | A45D 1/04 219/201 |

FOREIGN PATENT DOCUMENTS

JP    2012000630 A   *   1/2012   ............. B23K 26/20

* cited by examiner

*Primary Examiner* — Christopher S Kelley
*Assistant Examiner* — Asmamaw G Tarko
(74) *Attorney, Agent, or Firm* — NSIP Law

(57) ABSTRACT

Disclosed herein are a system of measuring a warpage and a method of measuring a warpage. The system of measuring a warpage of a sample by analyzing an image photographed by the camera using light that is diffused from a light source and reflected on a surface of a sample and is arrived at the camera through a reference grating part, the system includes: an intake part that removes a fume generated from the sample. By this configuration, it is possible to measure the warpage while effectively removing the fume generated from the sample according to the increase in the temperature of the sample at the time of measuring the warpage, thereby improving the accuracy of the warpage measurement.

11 Claims, 8 Drawing Sheets

- PRIOR ART -

- PRIOR ART -

SYSTEM OF MEASURING WARPAGE AND METHOD OF MEASURING WARPAGE

CROSS REFERENCE(S) TO RELATED APPLICATIONS

This application claims the benefit under 35 U.S.C. Section 119 of Korean Patent Application Serial No. 10-2012-0113554 entitled "System of Measuring Warpage and Method of Measuring Warpage" filed on Oct. 12, 2012, which is hereby incorporated by reference in its entirety into this application.

BACKGROUND OF THE INVENTION

1. Technical Field

The present invention relates to a system of measuring a warpage and a method of measuring a warpage.

2. Description of the Related Art

Recently, a demand for miniaturization and slimness of electronic products has increased. In order to meet the demand, attempts to make a substrate used as main parts of various electronic products smaller and thinner has continuously been conducted. Further, in order to implement high performance of electronic products, technologies for mounting active devices such as integrated circuit chips with high integration, and the like, and passive devices such as MLCC, inductor, and the like, in the inside or the outside of the substrate have been proposed.

Therefore, recently released package substrates have a duplex structure. Meanwhile, numerous micro circuit patterns are formed in the inside and outside of the package substrate and various electronic parts are embedded in the inside thereof or mounted on a surface thereof.

However, the complicated and slim package substrate products have reduced reliability due to a bending deflection phenomenon, that is, a warpage phenomenon according to the increase in temperature.

Therefore, a study for developing a technology of reducing the warpage, a technology of measuring how much the warpage is generated when the package substrate having a specific structure is exposed to the high temperature environment, and the like, have been conducted at various angles.

A representative method of the methods of measuring the warpage of the substrate may include a shadow moiré method introduced in Patent Document 1.

FIG. 1 is a diagram for describing a general measuring principle according to the related art that measures warpage using the shadow moiré method and FIG. 2 is a diagram schematically illustrating a fringe image.

Referring to FIGS. 1 and 2, an image reflected from a surface of a sample 2 by irradiating light using a light source 3 in the state in which a reference grating 1 arranged at a predetermined distance on a transparent quart panel and rendered as a reference line is disposed on a measuring sample 2 is acquired by a camera 4. In this case, the acquired image is formed with a fringe as illustrated in FIG. 2, such that it can measure how much the sample is warped based on the analysis of the fringe.

Meanwhile, in order to acquire the fringe image by using the shadow moiré method, light needs to be diffused-reflected from the surface of the sample.

Therefore, a sample pre-treating process is required in order to make the surface of the sample as the diffused reflection surface, which is performed by a process of thinly applying white spray on the surface of the sample.

However, the temperature of the sample is increased to about 260° C. by a heating plate 5, and the like, at the time of measuring the high temperature warpage. In this case, a fume is generated from a white spray material due to the high temperature.

The surface of the reference grating 1 is polluted due to the fume and thus, a contrast is the measured image is remarkably degraded, causing a problem in that the warpage cannot be accurately analyzed.

RELATED ART DOCUMENT

Patent Document (Patent Document 1) U.S. Pat. No. 7,230,722

SUMMARY OF THE INVENTION

An object of the present invention is to provide a system of measuring a warpage capable of removing a fume generated from a sample and photographing an image.

Another object of the present invention is to provide a method of measuring a warpage capable of reducing a measuring error of a warpage due to a fume generated from a sample.

According to an exemplary embodiment of the present invention, there is provided a system of measuring a warpage, including: a light source that irradiates light reflected from a surface of a sample of which the warpage is measured; a heating plate part having the sample disposed thereon and diffusing heat; a reference grating part that is spaced apart from the sample at a predetermined distance and transmits light reflected from the surface of the sample; a camera that acquires light transmitting the reference grating part to photograph an image; a server that analyzes the image photographed by the camera to calculate the warpage of the sample; and a control part provided with an intake part that removes a fume generated from the sample, wherein the reference grating part includes: a reference grating plate in which grids are formed on a transparent plate at a predetermined distance; a frame that fixes the reference grating plate; and at least one first suction hole that is mounted in the frame and is connected with the intake part by a first exhaust pipe.

The control part may further include a temperature control part that is connected with the heating plate part to control a temperature of the heating plate part.

The control part may further include a distance control part that is connected with the reference grating part to control a distance between the reference grating part and the heating plate part.

According to another exemplary embodiment of the present invention, there is provided a system of measuring a warpage, including: a light source that irradiates light reflected from a surface of a sample of which the warpage is measured; a heating plate part having the sample disposed thereon and diffusing heat; a reference grating part that is spaced apart from the sample at a predetermined distance and transmits light reflected from the surface of the sample; a camera that acquires light transmitting the reference grating part to photograph an image; a server that analyzes the image photographed by the camera to calculate the warpage of the sample; and a control part provided with an intake part that removes a fume generated from the sample, wherein the heating plate part includes: a body part that supports the sample and generates heat; and at least one second suction hole that is mounted in the body part and is connected with the intake part by a second exhaust pipe.

The control part may further include a temperature control part that is connected with the heating plate part to control a temperature of the heating plate part.

The control part may further include a distance control part that is connected with the reference grating part to control a distance between the reference grating part and the heating plate part.

According to still another exemplary embodiment of the present invention, there is provided a system of measuring a warpage of a sample by analyzing an image photographed by the camera using light that is diffused from a light source and reflected on a surface of a sample and is arrived at the camera through a reference grating part, the system including: an intake part that removes a fume generated from the sample.

The reference grating part may include a reference grating plate in which grids are formed on a transparent plate at a predetermined distance; and a frame that fixes the reference grating plate and is provided with at least one first suction hole, and a first exhaust pipe may be mounted between the first suction hole and the intake part.

The system of measuring a warpage may further include: a heating plate part that is provided with a body part supporting the sample and generating heat and at least one second suction holes mounted on the body part, and supports the sample, wherein a second exhaust pipe is mounted between the second suction hole and the intake part.

The sample may be disposed at a center of the body part and the second suction hole may be provided at an outside of the body part and may be spaced apart from the sample at a predetermined distance.

According to still yet another exemplary embodiment of the present invention, there is provided a method of measuring a warpage of a sample by analyzing an image photographed by the camera at which light diffused from a light source and reflected on a surface of a sample is arrived at the camera through a reference grating part, the method including: photographing an image while removing a fume generated from the sample.

A fume generated from a sample may be removed through an intake part.

DESCRIPTION OF THE PREFERRED EMBODIMENTS

Figure 1:
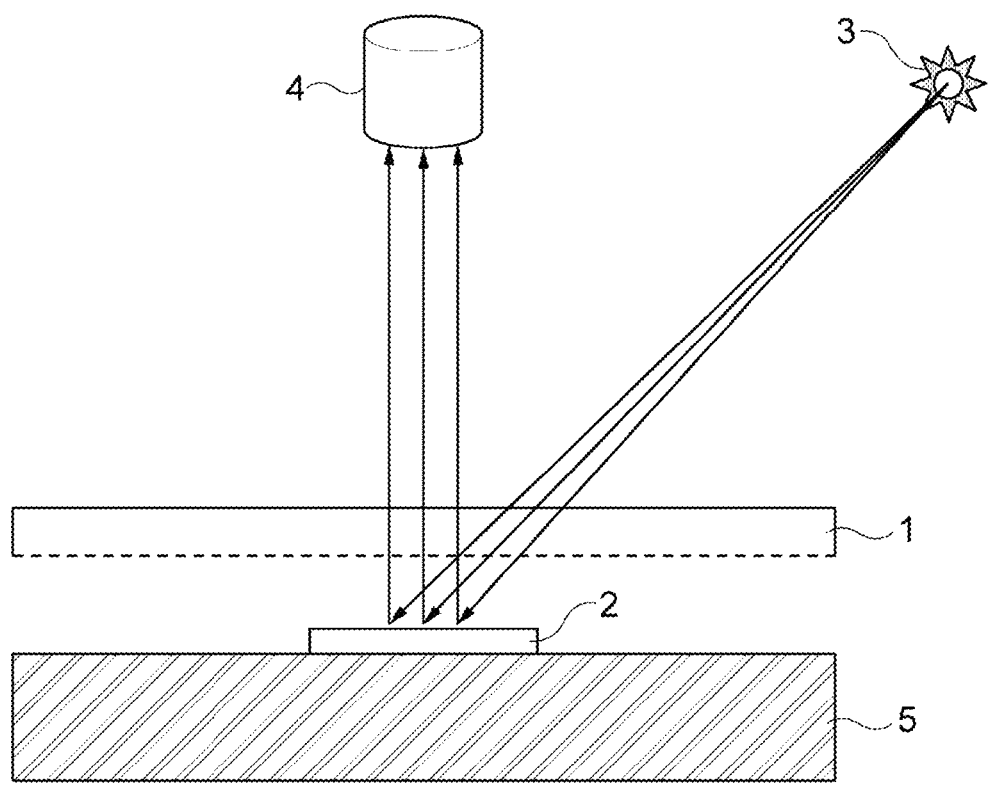
FIG. 1 is a diagram for describing a general measuring principle according to the related art for measuring a warpage using a shadow moiré method.

Various advantages and features of the present invention and methods accomplishing thereof will become apparent from the following description of embodiments with reference to the accompanying drawings. However, the present invention may be modified in many different forms and it should not be limited to the embodiments set forth herein. These embodiments may be provided so that this disclosure will be thorough and complete, and will fully convey the scope of the invention to those skilled in the art. Like reference numerals throughout the description denote like elements.

Terms used in the present specification are for explaining the embodiments rather than limiting the present invention. Unless explicitly described to the contrary, a singular form includes a plural form in the present specification. The word "comprise" and variations such as "comprises" or "comprising," will be understood to imply the inclusion of stated constituents, steps, operations and/or elements but not the exclusion of any other constituents, steps, operations and/or elements.

For simplification and clearness of illustration, a general configuration scheme will be shown in the accompanying drawings, and a detailed description of the feature and the technology well known in the art will be omitted in order to prevent a discussion of exemplary embodiments of the present invention from being unnecessarily obscure. Additionally, components shown in the accompanying drawings are not necessarily shown to scale. For example, size of some components shown in the accompanying drawings may be exaggerated as compared with other components in order to assist in understanding of exemplary embodiments of the present invention. Like reference numerals on different drawings will denote like components, and similar reference numerals on different drawings will denote similar components, but are not necessarily limited thereto.

In the specification and the claims, terms such as "first", "second", "third", "fourth" and the like, if any, will be used to distinguish similar components from each other and be used to describe a specific sequence or a generation sequence, but is not necessarily limited thereto. It may be understood that these terms are compatible with each other under an appropriate environment so that exemplary embodiments of the present invention to be described below may be operated in a sequence different from a sequence shown or described herein. Likewise, in the present specification, in the case in which it is described that a method includes a series of steps, a sequence of these steps suggested herein it not necessarily a sequence in which these steps may be executed. That is, any described step may be omitted and/or any other step that is not described herein may be added to the method.

In the specification and the claims, terms such as "left", "right", "front", "rear", "top, "bottom", "over", "under", and the like, if any, are not necessarily to indicate relative positions that are not changed, but are used for description. It may be understood that these terms are compatible with each other under an appropriate environment so that exemplary embodiments of the present invention to be described below may be operated in a direction different from a direction shown or described herein. A term "connected" used herein is defined as being directly or indirectly connected in an electrical or non-electrical scheme. Targets described as being "adjacent to" each other may physically contact each other, be close to each other, or be in the same general range or region, in the context in which the above phrase is used. Here, a phrase "in an exemplary embodiment" means the same exemplary embodiment, but is not necessarily limited thereto.

Hereinafter, a configuration and an acting effect of exemplary embodiments of the present invention will be described in more detail with reference to the accompanying drawings.

Figure 3:
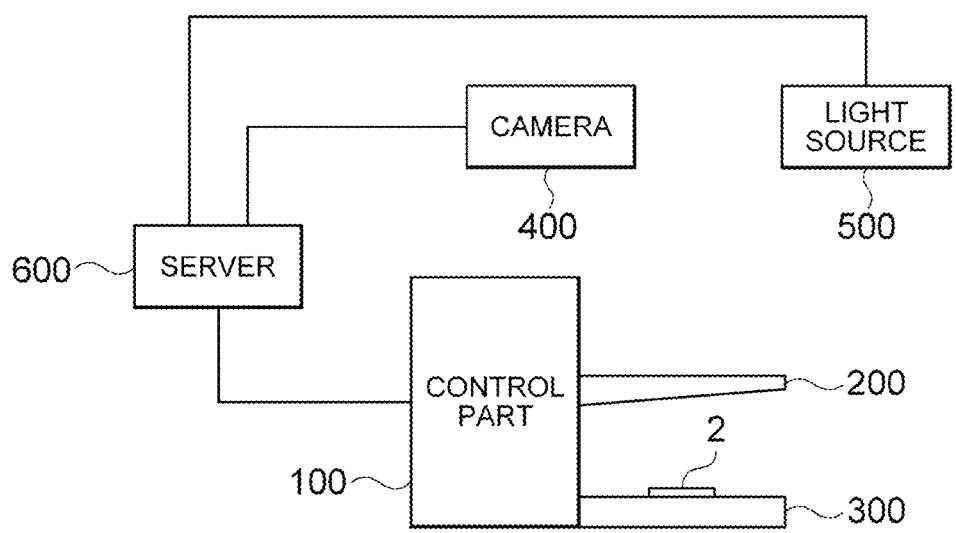
FIG. 3 is a diagram schematically illustrating a system of measuring a warpage according to an exemplary embodiment of the present invention.
Figure 4:
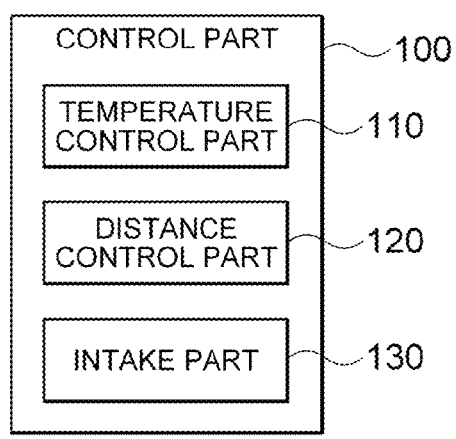
FIG. 4 is a diagram schematically illustrating a control part of FIG. 3.
Figure 5A:
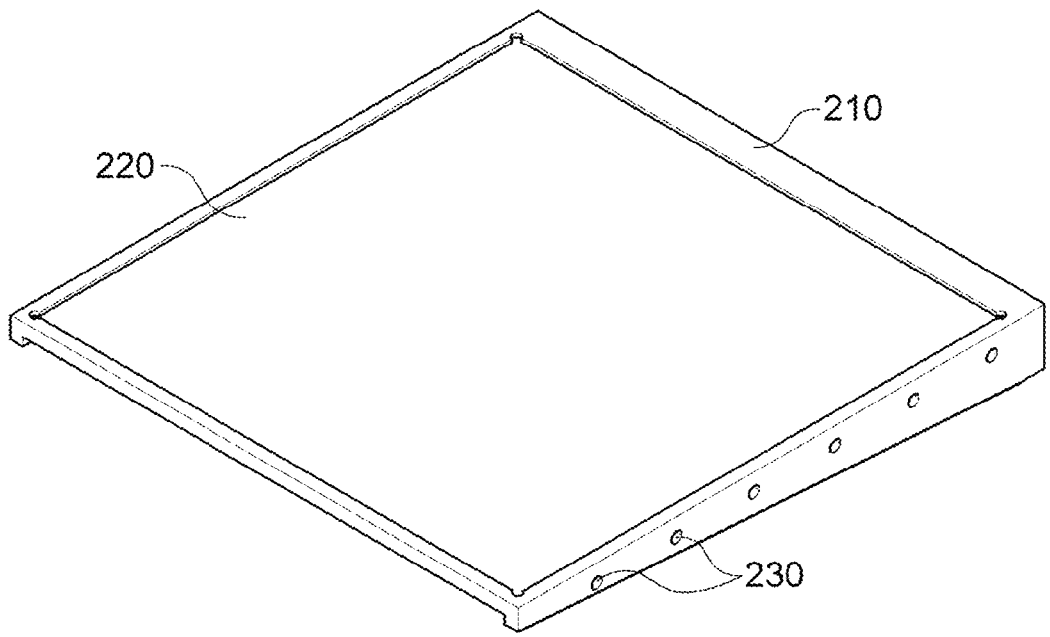
FIG. 5A is a perspective view schematically illustrating a reference grating part according to the exemplary embodiment of the present invention.
Figure 5B:
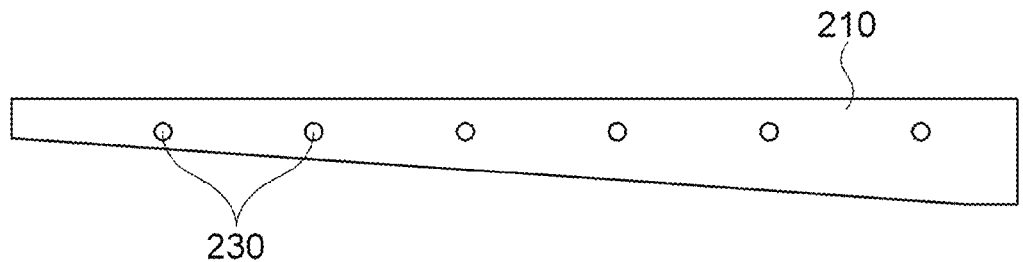
FIG. 5B is a side view schematically illustrating the reference grating part according to the exemplary embodiment of the present invention.
Figure 5C:
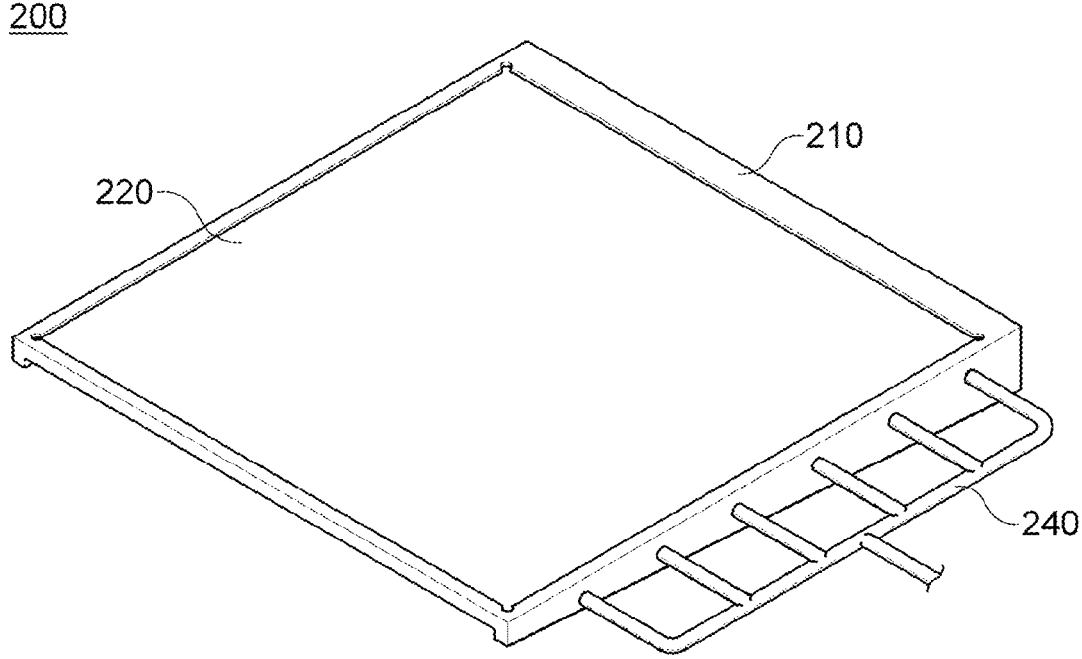
FIG. 5C is a perspective view schematically illustrating a state in which the reference grating part according to the exemplary embodiment of the present invention is coupled with a first exhaust pipe.

FIG. 3 is a diagram schematically illustrating a system 1000 of measuring a warpage according to an exemplary embodiment of the present invention, FIG. 4 is a diagram schematically illustrating a control part 100 of FIG. 3, FIG. 5A is a perspective view schematically illustrating a reference grating part 200 according to an exemplary embodiment of the present invention, FIG. 5B is a side view schematically illustrating the reference grating part 200 according to the exemplary embodiment of the present invention, and FIG. 5C is a perspective view schematically illustrating a state in which the reference grating part 200 according to the exemplary embodiment of the present invention is coupled with a first exhaust pipe 240.

The system 1000 of measuring a warpage according to the exemplary embodiment of the present invention may measure a warpage of the sample 2 by analyzing an image photographed by the camera 400 using light that is diffused from a light source 500 and reflected on a surface of a sample 2 and is arrived at the camera 400 through the reference grating part 200.

Referring to FIGS. 3 to 5C, the system 1000 of measuring a warpage according to the exemplary embodiment of the present invention may include a light source 500, a heating plate part 300, a reference grating part 200, a camera 400, a server 600, and a control part 100.

First, the light source 500 serves to irradiate light to a sample 2 of which the warpage is measured.

The light provided to the sample 2 from the light source 500 is reflected from the surface of the sample 2 and some of the reflected light reaches the camera 400 through the reference grating part 200.

In this case, the camera 400 may be implemented by a general digital camera 400 such as a CCD camera 400, and the like, that collects light to acquire a predetermined image and outputs the acquired image in a digital data form.

Figure 2:
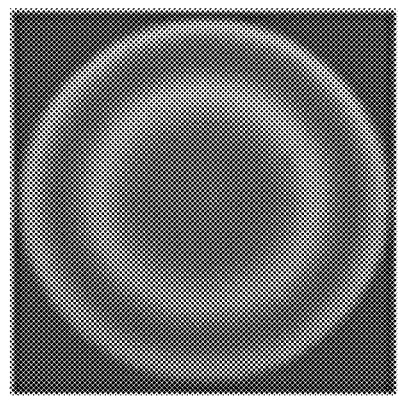
FIG. 2 is a diagram schematically illustrating a fringe image.

The data output from the camera 400 is transferred to a server 600 and the server 600 may calculate the warpage of the same 2 by applying a shadow moiré technique using a fringe image as illustrated in FIG. 2.

Meanwhile, the sample 2 may be disposed on the heating plate part 300, wherein the heating plate part 300 diffuses heat to heat the sample 2 so that the sample 2 reaches a predetermined temperature.

The reference grating part 200 is disposed in a path through which the reflected from the surface of the sample 2 reaches the camera 400 and may include a reference grating plate 220 in which grids are formed on a transparent plate of a material such as quartz, and the like, at a predetermined distance.

In this case, the reference grating part 200 needs to be supported so as to maintain a predetermined distance from the heating plate part 300. To this end, the reference grating plate 200 may further include a frame 210 for fixing the reference grating plate 220 at a predetermined position.

Further, the frame 210 may be provided with one or a plurality of first suction holes 230.

Meanwhile, as described above, white spray, and the like, is applied to the surface of the sample 2 so as to diffused-reflect light from the surface of the sample 2. When the white spray, and the like, generates a fume under the high temperature environment, the reference grating plate 220 is polluted due to the fume, such that image sharpness for measuring a warpage is degraded.

The present invention devised so as to solve the above problem includes an intake part 130 so as to remove a fume, wherein the intake part 130 may be connected with a first suction hole 230 of the frame 210 through the first exhaust pipe 240.

Meanwhile, as illustrated in FIGS. 3 and 4, the control part 100 may include a temperature control part 110, a distance control part 120, and an intake part 130.

First, the temperature control part 110 may be connected with the foregoing heating plate part 300 to control the temperature of the heating plate part 300.

That is, a heating element (not illustrated) such as heat rays, and the like, is included in the heating plate part 300 and the heating element and the temperature control part 110 are electrically connected with each other to supply electric energy, thereby increasing the temperature of the heating plate.

Further, although not illustrated, the cooling of the sample 2 is performed by spraying nitrogen, and the like, to the sample 2, thereby reducing the temperature of the sample 2.

Meanwhile, a temperature sensor (not illustrated) that is connected with the temperature control part 110, if necessary, to measure the temperature of the sample 2 and the heating plate part 300 may be further provided.

Next, the distance control part 120 may be connected with the reference grating part 200 and may serve to control a distance between the reference grating part 200 and the heating plate part 300.

In this case, one portion of the frame 210 is connected with the distance control part 120 of control part 100 such that the position of the frame 210 may move. As such, when only one portion of the frame 210 is fixed to the distance control part 120, the other of the frame 210 is not separately supported and thus, the problems due to torque may be caused. Therefore, a thickness of the frame 210 at a portion which is fixed to the distance control part 120 may be smaller than that of the other portion of the frame 210.

Next, the intake part 130 is connected with the first suction hole 230 through the first exhaust pipe 240 to suck and discharge the fume generated from the sample 2, thereby preventing the reference grating part 200 from being polluted.

In this case, the control part 100 is connected with the server 600 to receive a distance condition, a temperature condition, and the like, that are required for measurement.

Generally, when intending to measure the high temperature warpage for the sample 2 such as the substrate, the package, and the like, the measurement is performed by a temperature profile of 25° C.→260° C.→25° C. and the warpage data is analyzed by photographing each image in the state in which the temperature of the sample 2 is changed at an interval of 5° C. or 10° C.

Further, as an example, the warpage may be calculated by taking a photograph in the state in which the reference grating parts 200 are each disposed so that a distance between the reference grating part 200 and the heating plate part 300 is 100 mm, 105 mm, 110 mm, and 115 mm under the same temperature condition. In this case, a process of controlling the distance between the reference grating part 200 and the heating plate part 300 may be performed by the foregoing distance control part 120.

Meanwhile, the fume is generated from the sample 2 or the white spray on the surface of the sample 2 from about 200° C. and is deposited in the transparent reference grating part 200, such that the reference grating part 200 starts to be polluted.

The generation of the fume is more generated as the temperature of the sample 2 is increased.

Figure 9:
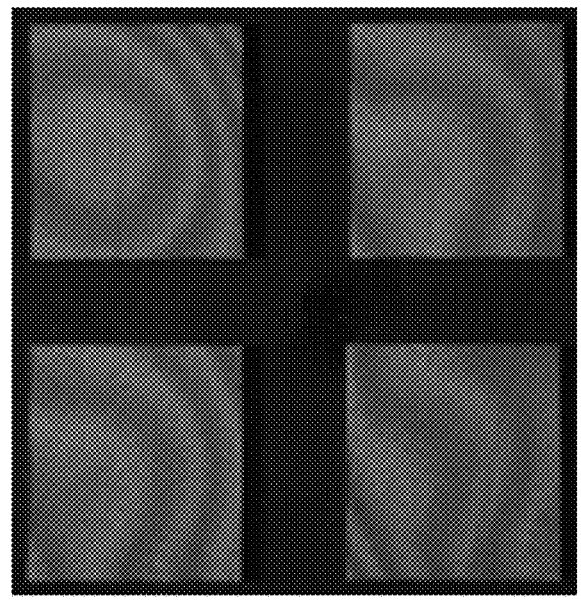
FIG. 9 is a diagram schematically illustrating a fringe image acquired in a state in which the reference grating is not polluted.
Figure 10:
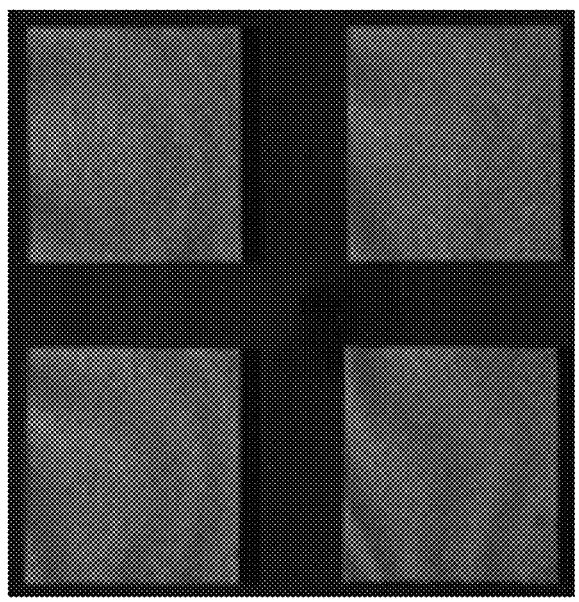
FIG. 10 is a diagram schematically illustrating a fringe image acquired in a state in which the reference grating is polluted.

FIG. 9 is a diagram schematically illustrating the acquired fringe image in the state in which the reference grating is not polluted and FIG. 10 is a diagram schematically illustrating the acquired fringe image in the state in which the reference grating is polluted.

Referring to FIGS. 9 and 10, it can be appreciated that the warpage cannot be precisely measured using only the image acquired in the state in which the reference grating part 200 is polluted due to the fume.

In this case, the fringe image of FIG. 9 may be an image photographed by the system 1000 of measuring a warpage according to the exemplary embodiment of the present invention and may be an image photographed by the general apparatus of measuring a warpage in the state in which the sample 2 is not heated, that is, in the state in which the fume is not generated and thus, the reference grating is not polluted.

Figure 6A:
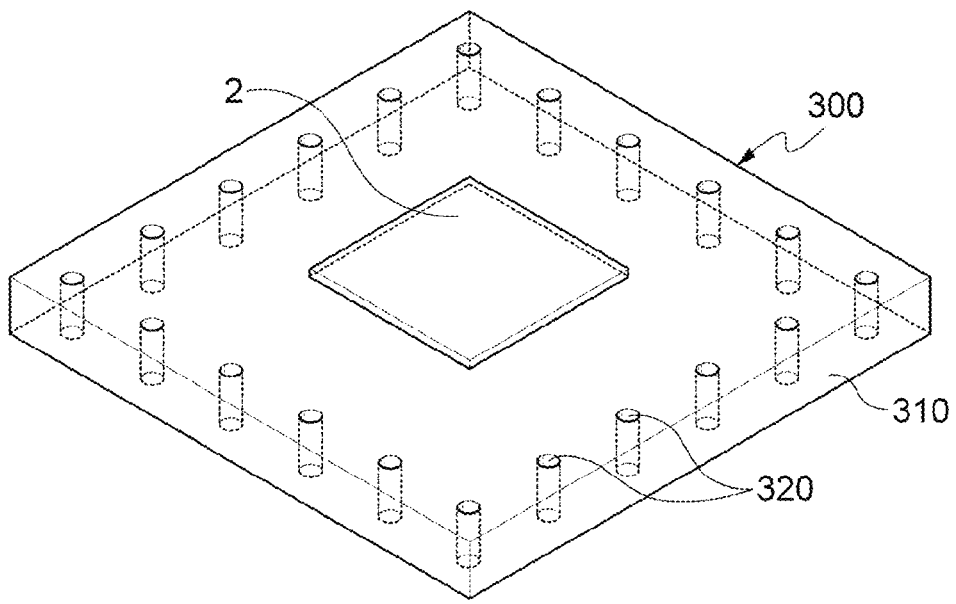
FIG. 6A is a perspective view schematically illustrating a heating plate part according to another exemplary embodiment of the present invention.
Figure 6B:
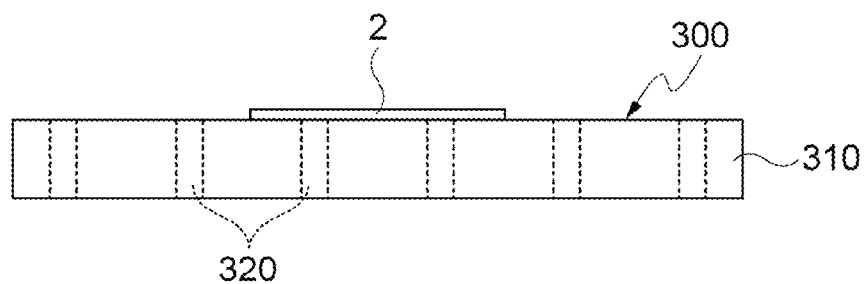
FIG. 6B is a side cross-sectional view schematically illustrating the heating plate part according to another exemplary embodiment of the present invention.
Figure 6C:
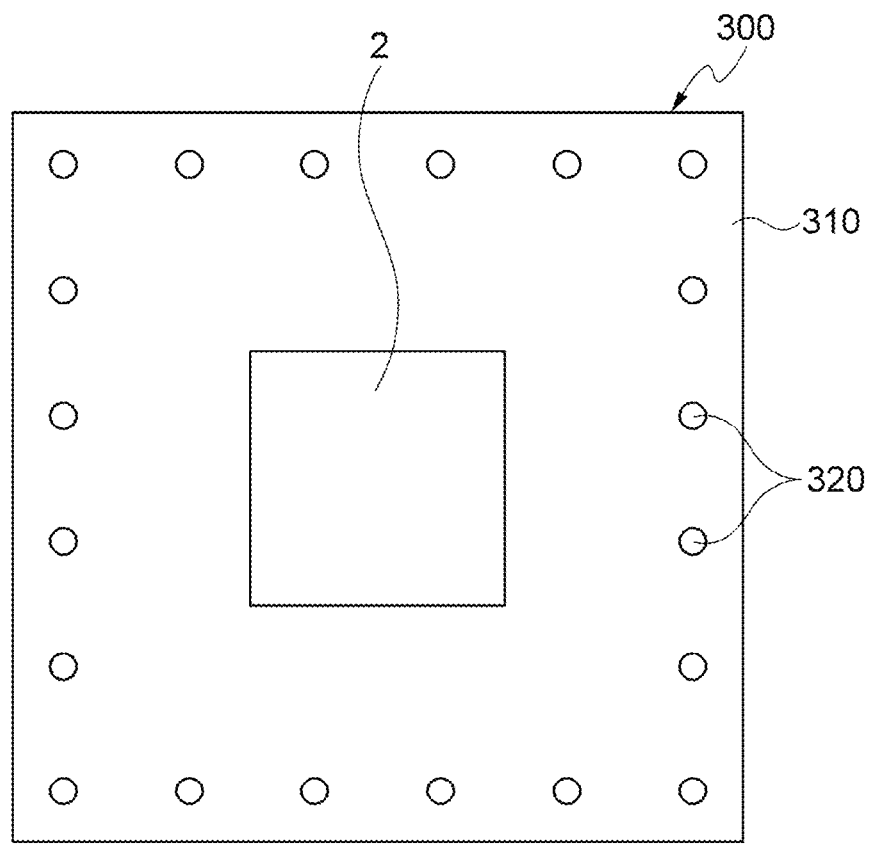
FIG. 6C is a plan view schematically illustrating the heating plate part according to another exemplary embodiment of the present invention.
Figure 6D:
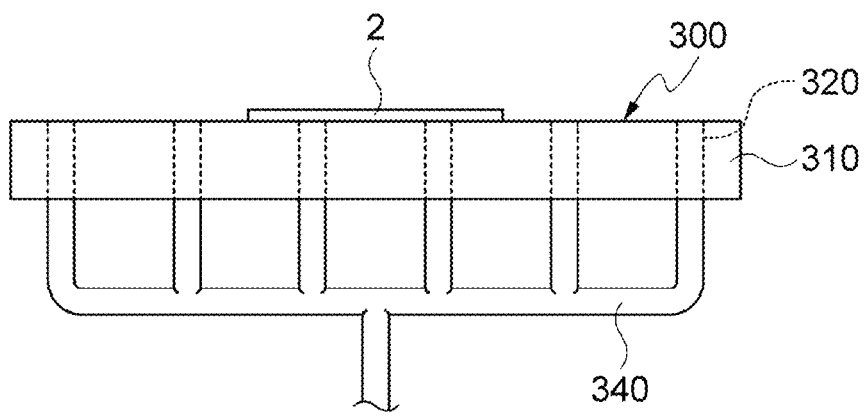
FIG. 6D is a side cross-sectional view schematically illustrating a state in which the heating plate part according to another exemplary embodiment of the present invention is coupled with a second exhaust pipe.

FIG. 6A is a perspective view schematically illustrating the heating plate part 300 according to another exemplary embodiment of the present invention, FIG. 6B is a side cross-sectional view schematically illustrating the heating plate part 300 according to another exemplary embodiment of the present invention, FIG. 6C is a plan view schematically illustrating the heating plate part 300 according to another exemplary embodiment of the present invention, and FIG. 6D is a side cross-sectional view schematically illustrating a state in which the heating plate part 300 according to another exemplary embodiment of the present invention is coupled with a second exhaust pipe 340.

Unlike the foregoing exemplary embodiment, in the system 1000 of measuring a warpage according to the present embodiment, the heating plate part 300 may be provided with a second suction hole 320 to remove a fume.

That is, the heating plate part 300 may include a body part 310 and the second suction hole 320. In this case, the body part 310 supports the sample 2 to generate heat and the second suction hole 320 may be connected with the intake part 130 by the second exhaust pipe 340.

Therefore, the fume between the surface of the sample 2 and the reference grating part 200 is discharged through the second suction hole 320, thereby removing the fume.

Other matters are similar to the description of the foregoing exemplary embodiments and the overlapping description will be omitted.

Figure 7:
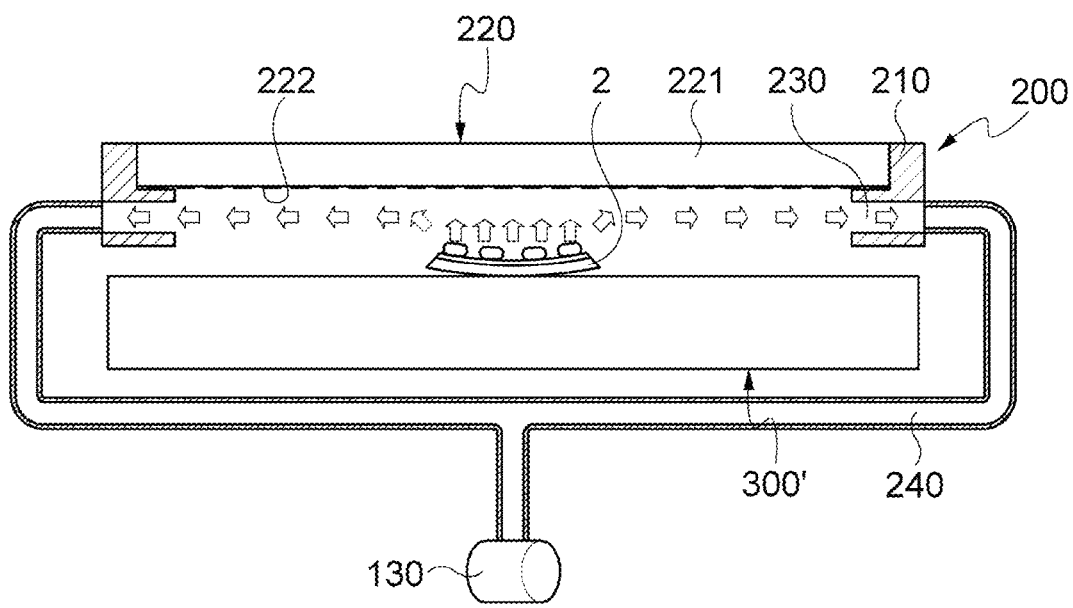
FIG. 7 is a diagram for describing a principle of removing a fume of a system of measuring a warpage according to the exemplary embodiment of the present invention.
Figure 8:
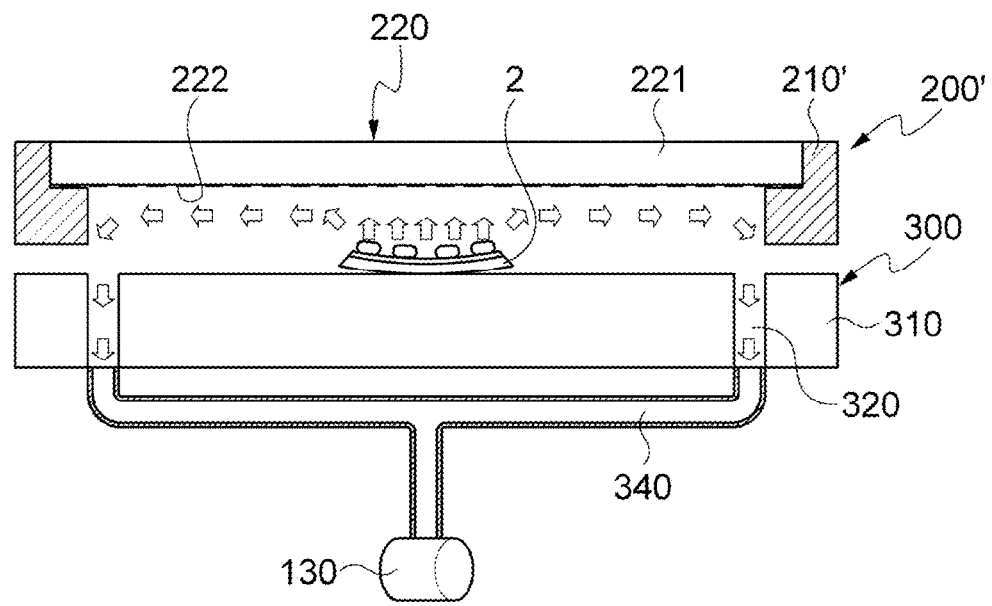
FIG. 8 is a diagram for describing a principle of removing a fume of a system of measuring a warpage according to another exemplary embodiment of the present invention.

FIG. 7 is a diagram for describing a principle of removing a fume of the system 1000 of measuring a warpage according to the exemplary embodiment of the present invention and FIG. 8 is a diagram for describing a principle of removing a fume of the system 1000 of measuring a warpage according to another exemplary embodiment of the present invention.

Referring to FIGS. 7 and 8, when the first suction hole 230 is formed in the reference grating part 200 (FIG. 7) or the second suction hole 320 is formed in the heating plate part 300 (FIG. 8), it can be appreciated that the fume generated from the sample 2 may be discharged through the first suction hole 230 and the first exhaust pipe 240 or may be discharged through the second suction hole 320 and the second exhaust pipe 340 before the fume pollutes the reference grating part 200.

Meanwhile, the sample 2 is more warped as the sample 2 is exposed to the high temperature environment. In this case, since the second suction hole 320 is too close to the sample 2, the sample 2 may be shaken when air is sucked at high pressure and therefore, it is preferable to form the second suction hole 320 while securing a predetermined gap between an area in which the sample 2 is disposed and the second suction hole 320.

Similarly, when an area of the reference grating part 200 is relatively small, the sample 2 may be shaken due to a flow of air sucked into the first suction hole 230 mounted in the frame 210 and therefore, it is preferable to form the area of the reference grating part 200 to be larger as much as a predetermined ratio than that of the sample 2.

Meanwhile, although not illustrated, the reference grating part 200 and the heating plate part 300 are suction holes, thereby rapidly removing the fume.

Further, the intake part 130 is actuated from the time when the temperature of the heating plating part 300 is higher than the temperature at which the fume is generated and may include a separate fume detecting sensor (not illustrated) to be actuated when the fume is detected.

As set forth above, according to the exemplary embodiments of the present invention, it is possible to measure the warpage while effectively removing the fume generated from the sample according to the increase in the temperature of the sample at the time of measuring the warpage, thereby improving the accuracy of the warpage measurement.

As described above, the present invention will be described with reference to the exemplary embodiments, but is not limited thereto. It can be apparent to those skilled in the art that the exemplary embodiments of present invention can be variously changed and applied within the scope of the present invention without departing from the technical idea of the present invention. Therefore, the protection scope of the present invention must be construed by the appended claims and it should be construed that all spirits within a scope equivalent thereto are included in the appended claims of the present invention.

What is claimed is:

1. A system of measuring a warpage, comprising:
   a light source that irradiates light reflected from a surface of a sample of which the warpage is measured;

a heating plate part having the sample disposed thereon and diffusing heat;

a reference grating part that is spaced apart from the sample at a predetermined distance and transmits light reflected from the surface of the sample;

a camera that acquires light transmitting the reference grating part to photograph an image;

a server that analyzes the image photographed by the camera to calculate the warpage of the sample; and a control part provided with an intake part that removes a fume generated from the sample, wherein the reference grating part includes:

a reference grating plate in which grids are formed on a transparent plate at a predetermined distance;

a frame that fixes the reference grating plate; and at least one first suction hole that is mounted in the frame and is connected with the intake part by a first exhaust pipe.

2. The system according to claim 1, wherein the control part further includes a temperature control part that is connected with the heating plate part to control a temperature of the heating plate part.

3. The system according to claim 1, wherein the control part further includes a distance control part that is connected with the reference grating part to control a distance between the reference grating part and the heating plate part.

4. A system of measuring a warpage, comprising: a light source that irradiates light reflected from a surface of a sample of which the warpage is measured;

a heating plate part having the sample disposed thereon and diffusing heat;

a reference grating part that is spaced apart from the sample at a predetermined distance and transmits light reflected from the surface of the sample;

a camera that acquires light transmitting the reference grating part to photograph an image;

a server that analyzes the image photographed by the camera to calculate the warpage of the sample; and a control part provided with an intake part that removes a fume generated from the sample, wherein the heating plate part includes:

a body part that supports the sample and generates heat; and at least one second suction hole that is mounted in the body part and is connected with the intake part by a second exhaust pipe.

5. The system according to claim 4, wherein the control part further includes a temperature control part that is connected with the heating plate part to control a temperature of the heating plate part.

6. The system according to claim 4, wherein the control part further includes a distance control part that is connected with the reference grating part to control a distance between the reference grating part and the heating plate part.

7. A system of measuring a warpage of a sample by analyzing an image photographed by a camera using light that is diffused from a light source and reflected on a surface of a sample and is arrived at the camera through a reference grating part, the system comprising:

an intake part that removes a fume generated from the sample, wherein the reference grating part includes:

a reference grating plate in which grids are formed on a transparent plate at a predetermined distance; and a frame that fixes the reference grating plate and is provided with at least one first suction hole, and a first exhaust pipe is mounted between the first suction hole and the intake part.

8. A system of measuring a warpage of a sample by analyzing an image photographed by a camera using light that is diffused from a light source and reflected on a surface of a sample and is arrived at the camera through a reference grating part, the system comprising:

an intake part that removes a fume generated from the sample; and a heating plate part that is provided with a body part supporting the sample and generating heat and at least one second suction hole mounted on the body part, and supports the sample, wherein a second exhaust pipe is mounted between the second suction hole and the intake part.

9. The system according to claim 8, wherein the sample is disposed at a center of the body part, and the second suction hole is provided at an outside of the body part and is spaced apart from the sample at a predetermined distance.

10. The system according to claim 7, further comprising:

a heating plate part that is provided with a body part supporting the sample and generating heat and at least one second suction hole mounted on the body part, and supports the sample, wherein a second exhaust pipe is mounted between the second suction hole and the intake part.

11. A method of measuring a warpage using the system of measuring a warpage according to claim 1 to photograph an image while removing a fume generated from a sample through an intake part.

* * * * *